United States Patent [19]

Tomibe et al.

[11] Patent Number: 5,049,684
[45] Date of Patent: * Sep. 17, 1991

[54] ELECTRICALLY CONDUCTING MATERIAL AND PROCESS OF PREPARING SAME

[75] Inventors: Shinji Tomibe, Kyoto; Reizo Gomibuchi, Uji; Kiyofumi Takahashi, Yawata, all of Japan

[73] Assignee: Nihon Sanmo Dyeing Co., Ltd., Kyoto, Japan

[*] Notice: The portion of the term of this patent subsequent to Dec. 21, 1999 has been disclaimed.

[21] Appl. No.: 414,650

[22] Filed: Sep. 3, 1982

Related U.S. Application Data

[63] Continuation-in-part of Ser. No. 260,129, May 4, 1981, Pat. No. 4,378,226, and a continuation-in-part of Ser. No. 183,639, Sep. 3, 1980, Pat. No. 4,410,493.

[30] Foreign Application Priority Data

Mar. 5, 1980 [JP] Japan .................. 55-28386
Jun. 3, 1980 [JP] Japan .................. 55-74752
Sep. 11, 1981 [JP] Japan .................. 56-144446

[51] Int. Cl.$^5$ .......... C07K 1/08; C08K 9/02; D01F 11/06; D06M 1/83; H01B 1/06; H01B 1/20

[52] U.S. Cl. ...................... 556/113; 8/624; 8/192; 8/127.6; 8/115.62; 8/115.54; 8/115.55; 8/DIG. 13; 8/DIG. 18; 252/521; 427/343; 428/85; 428/242; 428/283; 428/327; 428/361; 428/389; 428/402; 428/403; 428/407; 428/458; 428/463; 428/698; 523/200; 523/204

[58] Field of Search .......... 8/624, 115.5, 116.2, 8/127.6, DIG. 18, 192, 128.3, 115.54, 115.55, 115.62, DIG. 13; 428/361, 389, 402, 403, 407, 458, 463, 698; 556/113; 252/521

[56] References Cited

U.S. PATENT DOCUMENTS

| | | | |
|---|---|---|---|
| 2,743,991 | 5/1956 | Schoonover et al. | 8/624 |
| 2,749,210 | 6/1956 | Sherrill . | |
| 2,779,726 | 1/1957 | Rochester | 8/624 |
| 3,014,818 | 12/1961 | Campbell . | |
| 3,416,874 | 12/1968 | Robin | 8/624 |
| 3,790,341 | 2/1974 | Makhkamov et al. | 8/624 |
| 3,840,389 | 10/1975 | Kobylinski et al. | 427/333 |
| 3,940,533 | 2/1976 | Arsac | 428/225 |
| 3,958,066 | 5/1976 | Imamura | 428/372 |
| 4,122,143 | 10/1978 | Momotari | 264/104 |
| 4,178,395 | 12/1979 | Jordan | 427/255.4 |
| 4,336,028 | 6/1982 | Tomibe et al. | 8/624 |
| 4,364,739 | 12/1982 | Tomibe et al. . | |
| 4,378,226 | 3/1983 | Tomibe et al. . | |

FOREIGN PATENT DOCUMENTS

| | | |
|---|---|---|
| 74056 | 1/1893 | Fed. Rep. of Germany . |
| 2329484 | 11/1973 | Fed. Rep. of Germany . |
| 644429 | 6/1928 | France . |
| 55-51873 | 4/1980 | Japan . |
| 1372656 | 11/1974 | United Kingdom . |
| 1396072 | 5/1975 | United Kingdom . |
| 2078545 | 1/1982 | United Kingdom . |

OTHER PUBLICATIONS

Schmidlin, Preparation and Dyeing of Synthetic Fiber, Chapman and Hall, London, 1963, p. 294.
Stille, J. Introduction to Polymer Chemistry, John Wiley & Sons, Inc., N.Y., pp. 172–174 (1967).
Kirk-Othmer Encyclopedia Of Chemical Technology, 2nd Ed., vol. 1, pp. 313–317, 324 and 327, John Wiley and Sons, New York (1963).

Primary Examiner—James C. Cannon
Attorney, Agent, or Firm—Fisher, Christen & Sabol

[57] ABSTRACT

An electrically conducting material including a cyanic group-containing material having adsorbed thereby copper sulfide. The cyanic group-containing material is in the form of powder or shaped body such as fiber, film, plate, rod or like and is formed of a synthetic polymer such as polyacrylonitrile or a polyamide having introduced thereinto cyanic groups; a naturally occurring polymeric substance such as cotton having introduced thereinto cyanic groups; or a low molecular compound such as phthalonitrile. The electrically conducting material may be prepared by treating the cyanic group-containing material with a source of monovalent copper ions and a sulfur-containing compound to form copper sulfide adsorbed by the cyanic group-containing material.

2 Claims, No Drawings

ELECTRICALLY CONDUCTING MATERIAL AND PROCESS OF PREPARING SAME

CROSS REFERENCE TO RELATED APPLICATIONS

This application is a continuation-in-part of our co-pending U.S. Ser. No. 183,639 filed Sept. 3, 1980, now U.S. Pat. No. 4,410,593 and a continuation-in-part of our co-pending U.S. Ser. No. 260,129 filed May 4, 1981, now U.S. Pat. No. 4,378,226.

BACKGROUND OF THE INVENTION

1. Field of the Invention

This invention relates generally to electrically conducting materials and, more specifically, to copper sulfide-carrying, electrically conducting materials. This invention is also directed to a process for the preparation of such electrically conducting materials.

2. Description of the Prior Art

Numerous methods for imparting electrical conductivity to synthetic polymeric materials in the form of a shaped body are known in the art. For example, in U.S. Pat. No. 3,940,533 issued to Arsac, there is proposed one method for imparting electrical conductivity to polymeric shaped materials such as polyamide fibers, in which the fibers are first contacted with hydrogen sulfide and the resulting fibers having the hydrogen sulfide impregnated therewithin are then immersed in a metal salt solution such as an aqueous copper sulfate solution, to form a deposit of metal sulfide, such as copper sulfide, on the fibers. This process, however, is not applicable to acrylic fibers. Moreover, the washability of the copper sulfide deposited fibers obtained according to this process has been found to be unsatisfactory.

SUMMARY OF THE INVENTION

The present invention provides an electrically conducting material which comprises a cyanic group-containing material having adsorbed thereby copper sulfide. Any cyanic group-containing substances may be used as the starting material so far as it is a water-insoluble solid. The starting cyanic group-containing material may be in the form of a shaped body such as fiber, film, block, plate or granule as well as in the form of powder. Not only acrylonitrile-series polymeric materials but also other synthetic or naturally occurring polymeric materials having introduced therein cyanic groups may be used as the starting material. In addition, low molecular weight compounds having one or more cyanic groups can be used as the cyanic group-containing material to which an electrical conductivity is imparted.

The electrically conducting material of this invention, when in the form of fibers, may be advantageously utilized as clothes, carpets, interior decorative sheets, gloves or like by themselves or in combination with other fibers because of their freeness of static charging and easiness to be dyed. When, in the form of a film or plate, the electrical conductivity and transparency of the materials of this invention allow the use thereof as a cover or enclosure for electric parts such as integrated circuits and large-scale integrated circuits which are required to be shielded from electrostatic charges during storage or transportation. The powdery, electrically conductive material of this invention may be incorporated into a coating composition to form electrically conductive coatings. Because of the excellent thermal stability of the copper sulfide, the powdery or granular, electrically conductive material of this invention formed from synthetic polymers, such as polyacrylonitrile, can be subjected to thermal molding conditions to produce electrically conducting molded articles. Further, the electrically conducting materials have been found to effectively absorb infrared rays with a wavelength of about 800 nm to 100 $\mu$m. Thus, the electrically conducting materials of this invention lend themselves to numerous applications in many fields.

In another aspect, the present invention provides a process for the preparation of the above electrically conducting materials. The process includes treating a cyanic group-containing material with a source of monovalent copper ions and a sulfur-containing compound to adsorb copper sulfide by the cyanic group-containing material. The treatment with the sulfur-containing compound may be subsequent to or simultaneous with the treatment with the monovalent copper ions.

It is, therefore, an object of the present invention to provide an electrically conducting material having excellent electrical conductivity and washability.

Another object of the present invention is to provide a simple process which can impart excellent electrical conductivity to cyanic group-containing materials.

Other objects, features and advantages of the present invention will become apparent from the detailed description of the invention to follow.

DETAILED DESCRIPTION OF THE INVENTION

The cyanic group-containing material used as the starting material includes both polymeric and low molecular substances. The cyanic group-containing polymeric substances involve both natural and synthetic polymers.

Not only acrylonitrile-series polymeric substances such as polymers and copolymers of acrylonitrile but also other polymeric substances such as polyamides and polyesters having introduced thereinto cyanic groups may be used as the starting synthetic polymers. The introduction of cyanic radicals into such synthetic polymers may be done by any known method such as by reaction with dicyandiamide, graft polymerization of acrylonitrile onto the polymers, cyanoethylization, mixed spinning, graft polymerized material spinning, blocked polymerized material spinning and the like. The starting synthetic polymers to be imparted with electrical conductivity may be in the form of powder or in the form of a shaped body such as a film, plate, fiber, fabric, paper, sheet, block, pellet, thread, rod or pipe.

The cyanic group-containing natural polymeric materials include polypeptides and polysaccharides, such as wool, silk and cotton, having introduced thereinto cyanic radicals. The introduction of cyanic radicals into such naturally occurring polymeric materials may be done by any known ways such as exemplified above. The cyanic group-containing natural polymers may be used in the form of powder of fibers.

Illustrative of the cyanic group-containing low molecular compounds are phthalonitrile, isophthalonitrile, N-cyanomethylaniline and N-$\beta$-cyanoethylaniline. These compounds are generally used in the form of powder.

The above-described cyanic group-containing starting material is subjected to a treatment with a source of monovalent copper ions and a sulfur-containing compound at a temperature and for a period of time sufficient to form copper sulfide adsorbed on and/or within the starting material. The treatment with the sulfur-containing material may be simultaneous with or subsequent to the treatment with the source of monovalent copper ions.

As the source of monovalent copper ions, a combination of a bivalent copper compound, such as a salt or a complex of bivalent copper, and a reducing agent capable of converting the bivalent copper compound into monovalent copper ions is generally employed. Illustrative of the bivalent copper salts are cupric sulfate, cupric chloride, cupric nitrate and cupric acetate. Examples of the reducing agent include metallic copper, hydroxylamine or its salt, ferrous sulfate, ammonium vanadate, furfural, sodium hypophosphite and glucose. In some cases, cuprous salts may be used as the source of monovalent copper ions.

The sulfur-containing compound used in the process of this invention is of a type which is capable of providing sulfur atoms and/or sulfur ions for reaction with the copper ions to form copper sulfide which is adsorbed on or within the cyanic groupcontaining material. Illustrative of the sulfur-containing materials are sodium sulfide, sulfur dioxide, sodium hydrogen sulfite, sodium pyrosulfite, sulfurous acid, dithionous acid, sodium dithionite, sodium thiosulfate, thiourea dioxide, hydrogen sulfide, sodium formaldehyde sulphoxylate (rongalite C), zinc formaldehyde sulphoxylate (rongalite Z) and mixtures thereof. Since these sulfur-containing compounds have a reducing activity, they may be used as at least a part of the reducing agent for converting bivalent copper ions into mcnovalent ones.

When the treatments with the source of monovalent copper ions and with the sulfur-containing compound are simultaneous, the cyanic group-containing material to be treated is immersed in a bath containing the source of monovalent copper ions and the sulfur-containing compound preferably at a temperature of 20° to 150° C., more preferably 30° to 100° C. for a period of time 1 to 24 hours. When the reaction is conducted at an elevated temperature, it is preferred that the bath be heated at a rate of 1° to 3° C./min. The pH of the bath is preferably controlled to be in the range of about 1.5 to 6, more preferably 3 to 5. For this purpose, a pH controlling agent may be used. Examples of the pH controlling agent include inorganic acids such as sulfuric acid, hydrochloric acid and phosphoric acid; organic acids such as citric acid and acetic acid; and mixtures thereof. It is possible to carry out the treatment at a low temperature when the pH is low. When a gaseous sulfur-containing compound such as sulfur dioxide or hydrogen sulfide is used, it is bubbled through a solution containing the source of monovalent copper ions with the cyanic group-containing material being immersed therein.

In the embodiment of the present invention wherein the treatment with the sulfur-containing compound is preceded by the treatment with the source of monovalent copper ions, the cyanic group-containing material is first immersed in a first bath containing the source of monovalent copper ions preferably at a temperature of 50° to 150° C., more preferably 80° to 110° C. for a period of time so that monovalent copper ions are adsorbed by the cyanic group-containing material (first stage). The reaction time is generally 0.5 to 2 hours. The pH of the first bath is preferably controlled in the range of .1 to 3 with the use of such a pH controlling agent as described above. The cyanic group containing material from the first stage having the adsorbed monovalent copper ions is then treated in a second bath containing the sulfur-containing compound (second stage). Preferably, the treated material from the first stage is washed with a suitable liquid such as water prior to the second treatment stage. The treatment of the second stage is carried out preferably at a temperature of 50° to 120° C., more preferably 70° to 100° C. The reaction time generally ranges from 1.5 to 4.5 hours. It is preferable to gradually heat the bath at a. rate of 1° to 3° C./min. In the case where the second stage employs a gaseous sulfur-containing compound, the treated material from the first stage is contacted therewith at a pressure of 0.5 to 3 atm. at a temperature of 90° to 120° C. for 1 to 3 hours.

In both the above single and two-stage treatments, the amount of the source of monovalent copper ions varies according to the intended degree of electrical conductivity the content of cyanic groups in the starting material the form of the starting material and the like. Generally, thesource of monovalent copper ions is used in an amount of 2 to 15 g in terms of metallic copper per 100 g of the srarting cyanic group-containing material. The concentration of tne source of monovalent copper ions in the bath is generally 1 to 10 g/l in terms of elemental copper. The amount of sulfur-containing compound is generally 3 to 5 mol per mole of the monovalent copper ions.

The amount of copper sulfide to be adsorbed by the cyanic group-containing material is variable according to the object of the end use of the electrically conducting material. Generally, the amount of copper sulfide is 1 to 30% based upon the weight of the starting cyanic group-containing material.

The electrically conductive material of this invention is excellent in both electrical conductivity and fastness, i.e. it exhibits outstanding resistance to water, heat and physical abrasion. Therefore, the rate of the decrease in electrical conductivity during use is very low. Such excellent properties are considered to be partly ascribed to the fact that the copper sulfide is formed not only on the surface of the cyanic group-containing material but also within the material. Another and more important reason would be that the copper sulfide of the electrically conducting material contains a significant amount of as digenite ($Cu_9S_5$) and chalcocite ($Cu_2S$), which are far more stable than covellite ($Cu_9S_5$). Thus, it is preferred that the copper sulfide of the electrically conducting material exist mainly as $Cu_xS$ where x is about 1.8 to 2.0. According to the process of the present invention, it is possible to prepare electrically conducting materials wherein substantially all the copper sulfide may exist as $Cu_xS$ where x is about 1.8 to 2.0.

The following examples will further illustrate the present invention.

EXAMPLE 1

Cashmilon (acrylic fiber, 2 deniers, 51 millimeters in length of cut, type FWBR, made by Asahi Chemical Industry Co., Ltd., Japan) was heat-treated in an aqueous bath containing 30 wt. % of cupric sulfate, 4 wt. % of sulfuric acid, and 80 wt. % of copper net (No. 31, of a 12-mesh) in relation to the weight of the fiber in the bath. The weight ratio of the fiber weight to water weight containing the chemicals was 1:15. The heat-treatment was at a temperature of 95° C. for 60 minutes. Subsequently, the fiber was thoroughly washed in water. Next, the washed fiber was again heat-treated in an aqueous solution containing 10 grams of Rongalite C ($NaHSO_2$ $CH_2O \cdot 2H_2O$) and 1 milliliter of sulfuric acid in relation to 1 liter of water, at a temperature of 80° C. for 60 minutes. The electrically conducting fiber was dried after being washed in water for a second time. It had an olive-grey color, and contained 12.3 % by weight of copper sulfide in relation to the weight of the starting fiber. Its electrical resistivity was 0.085 $\Omega$-cm. The crystal structure of this electrically conducting fiber was analyzed by X-ray diffraction. The line of diffraction (interfacial distance: 1.97 U, 3.21 U, 2.79 U) was of digenite (empirical formula: $Cu_9S_5$)

When this electrically conducting fiber was subjected to the repeated washing test ten times according to Japanese Industrial Standards L-1045, A-2, its electrical resistivity was 0.090 $\Omega$-cm, and its washability was excellent.

This electrically conducting fiber was treated in an aqueous solution containing 2 % by weight of sumiacryl Brilliant Red N-4G (cationic dye, made by Sumitomo Chemical Industry Co., Ltd., Japan) in relation to the fiber weight at a temperature of 100° C. for 30 minutes. It was splendidly dyed a dark-red color without deterioration of its conductivity.

EXAMPLE 2

Example 1 was repeated except Rongalite Z ($ZnSO_2 \cdot CH_2O \cdot H_2O$) was used in place of Rongalite C. There was likewise obtained an electrically conducting fiber of the same nature as the fiber obtained in Example 1.

EXAMPLE 3

Kanekalon S (modacrylic fiber, 2 deniers, 51 millimeters in length of cut, made by Kanegafuchi Chemical Co., Ltd., Japan) was heat-treated in a bath containing 30 wt. % of cupric sulfate and 15 wt. % of hydroxylamine sulfate in relation to the weight of fiber in the bath. The ratio of the fiber weight to the water weight containing the chemicals was 1:15. The heat-treatment was at a temperature of 100° C. for 90 minutes. Next, the fiber was thoroughly washed in water. Then the washed fiber was again heattreated in an aqueous solution containing 10 grams of dithionous acid and 2 grams of sodium acetate in relation to 1 liter of water, at a temperature of 90° C. for 60 minutes. The electrically conducting fiber obtained after being thoroughly washed in water and dried had an olive-grey color and contained 10.8 % by weight copper sulfide in relation to the weight of the starting fiber. Its electrical resistivity was 0.86 $\Omega$-cm.

When this electrically conducting fiber was subjected to the repeated washing test ten times as in Example 1, deterioration of its conductivity was hardly perceived.

Further, this electrically conducting fiber was treated in an aqueous solution containing 2 wt. % of Diacryl Brilliant Blue H2R-N (cationic dye, made by Mitsubishi Chemical Industry Co., Ltd., Japan) in relation to the fiber weight at a temperature of 100° C. for 60 minutes. The electrically conducting fiber was splendidly dyed a dark-blue color.

EXAMPLE 4-7

The procedure of Example 3 is repeated except instead of dithionous acid either sodium dithionite, sodium thiosulfate, sodium hydrogen sulfite, or sodium pyrosulfite is used. In each case, there was obtained an electrically conducting fiber of the same nature as the fiber obtained in Example 3.

EXAMPLE 8

Toraylon (acrylic fiber, 3 deniers, 102 millimeters in length of cut, type T-106, made by Toray Industry, Inc., Japan) was heattreated in a bath containing 40 wt. % of cupric chloride and 20 wt. % of hydroxylamine sulfate in relation to the weight of fiber in the bath. The ratio of fiber weight to water weight containing the chemicals was 1:15. The heat-treatment was at a temperature of 100° C. for 60 minutes. Subsequently, the fiber was thoroughly washed in water. Next, the fiber thus washed was again heat-treated in an aqueous solution containing 15 grams of sodium sulfide and 4 milliliters of sulfuric acid in relation to 1 liter of water, at a temperature of 90° C. for 60 minutes. The electrically conducting fiber obtained after being thoroughly washed in water and dried had an olive-grey color and contained 15.1 % by weight copper sulfide in relation to the weight of the starting fiber. Its electrical resistivity was 0.060 $\Omega$-cm.

When this electrically conducting fiber was subjected to the repeated washing test ten times as in Example 1, deterioration of its conductivity was negligible.

Further, this electrically conducting fiber was treated in an aqueous solution containing 4 wt. % of Diacryl Navy Blue RL-N (cationic dye, made by Mitsubishi Chemical Industry Co., Ltd., Japan) in relation to the fiber weight, at a temperature of 100° C. for 60 minutes. Electrically conducting fiber dyed finely in a dark-blue color was obtained.

EXAMPLE 9

Cashmilon (acrylic fiber, 2 deniers, 51 millimeters in length of cut, made by Asahi Chemical Industry Co., Ltd., Japan) which was treated to adsorb monovalent copper ions through the same treatment as in Example 1 was put into a closed receptacle having a gas inlet. Sulfur dioxide was fed into the receptacle until the pressure in the interior thereof reached 0.5 $kg/cm^2$ gauge pressure. Then, saturated vapor at 105° C. was fed into the receptacle until the pressure within the receptacle reached 1.0 $kg/cm^2$ gauge pressure. After having shut the receptacle tightly, the fiber was caused to react therein. It was taken out after cooling, washed thoroughly in water, and dried. The electrically conducting fiber thus obtained had an olive-grey color. Its electrical resistivity was 0.50 $\Omega$-cm.

The electrically conducting fiber was tested for washability and dyeability by cationic dyestuffs. The results were as good as in the case of Examples 1 to 8.

EXAMPLE 10

Example 9 was repeated except hydrogen sulfide was used instead of sulfur dioxide. An electrically conducting fiber of the same nature as the fiber obtained in Example 9 was obtained.

EXAMPLE 11

Nylon staple (3 denier, cut length 76 mm, manufactured by Toray, Ltd.) is rinsed in warm water kept at a temperature of 50° C. to remove any oil and grease from it. Then, it is immersed in a bath which is a water solution comprising 50 wt. % of acrylonitrile, 1.2 wt. % of ammonium persulfate, and 3 wt. % of sodium hydrogen sulfite, based upon the weight of the nylon. The ratio of the nylon staple weight to the weight of the bath is 1:20. The bath is gradually heated up to 70° C. from room temperature and the fiber is treated at that temperature for 60 minutes. After that, it is rinsed well in warm water and then in cold water to remove any non-reacted matter, by-products, and catalysts, etc. from it completely. Upon analysis of the washed product, it was found that the graft polymerization ratio of acrylonitrile with said nylon staple was 10 %.

Next, the acrylonitrile grafted nylon staple is immersed in a bath which is a water solution comprising 10 wt. % of cupric sulfate, 10 wt. % of sodium thiosulfate, and 5 wt. % of sodium hydrogen sulfite, based upon the weight of the nylon. The ratio of the weight of the nylon staple to the weight of the bath is 1:20. The bath is gradually heated up to 100° C. from room temperature and is heated at that temperature for 60 minutes. After that, it is rinsed well in cold water and then is dried completely to obtain an olive-gray nylon staple.

Through X-ray analysis of the nylon staple obtained thereby, the line of diffraction (interfacial distance: 1.97 U, 3.21 U, and 2 79 U) was found to be of digenite, a form of copper sulfide (empirical formula: $Cu_9S_5$). The copper ions were dispersed through and adsorbed by said nylon staple in the form of copper sulfide.

Through measurement of the electrical resistivity of said olive-gray nylon staple, the resistivity was found to be $4 \times 10^{-1}$ Ω-cm and the content of copper sulfide impregnated into said nylon staple was found to be 3.5 % by weight.

EXAMPLE 12

Nylon staple impregnated with acrylonitrile as in Example 11 is immersed in a bath which is a water solution comprising 20 wt. % of cupric sulfate and 10 wt. % of hydroxylamine sulfate, based upon the weight of the nylon. The ratio of the weight of the nylon staple to the weight of the bath is 1:15. It is gradually heated up to 100° C. from room temperature and is treated at that temperature for 60 minutes. After the treatment, it is rinsed well in cold water.

After the rinsing step, the nylon staple is immersed in a bath which is a water solution comprising 10 g/l of sodium dithionite, 10 g/l of citric acid, and 22 g/l of disodium hydrogen phosphate. The bath is gradually heated up to 100° C. from room temperature. The nylon staple is treated at that temperature for 90 minutes. After the heat treatment, it is rinsed well in cold water and then dried completely.

The nylon staple obtained thereby has an olive-brown color and its electrical resistivity was found to be $8.5 \times 10^{-2}$ Ω-cm. The content of copper sulfide was found to be 6 % by weight.

EXAMPLE 13

Nylon BCF (1300 denier, 64 filaments, manufactured by Toyo Boseki, Ltd.) is cleaned to completely remove any oil and grease from it. Then, it is immersed in a bath which is a water solution comprising 50 wt. % of acrylonitrile, 1.2 wt. % of ammonium persulfate, and 3.0 wt. % of sodium hydrogen sulfite, based upon the weight of the nylon fiber. The ratio of the fiber weight to the water weight containing the chemicals was 1:20. The water solution was then gradually heated up to 70° C. from room temperature. The nylon was heat treated at that temperature for 60 minutes.

After the heat treatment, the fiber is rinsed well in cold water to completely remove any non-reacted matter, by-products, and catalysts.

Next, the cleaned fiber is immersed in a bath which is a water solution comprising 15 wt. % of cupric sulfate and 15 wt. % of sulfuric acid, based upon the weight of the fiber. The ratio of the fiber weight to the bath weight is 1:20. A copper sieve (No. 31, 12 meshes) in an amount of 80 % by weight of the fiber weight is added to the bath. Then, the water solution is gradually heated up to 100° C. from room temperature and the fiber is heat treated at that temperature for 60 minutes.

After the heat treatment, the fiber is immersed in a bath which is a water solution comprising 3.3 g/l sodium sulfide and 10 g/l of disodium hydrogen phosphate. The bath is gradually heated up to 90° C. from room temperature and kept at that temperature for 90 minutes.

The fiber obtained thereby has an olive-green color and its electrical resistivity was found to be $8.3 \times 10^{-1}$ Ω-cm. The content of copper sulfide was found to be 2.8 % by weight.

EXAMPLE 14

Polyester fiber (3 denier, cut length 80 mm bias, Type T-98 manufactured by Toray, Ltd.) is cleaned well and is immersed in a bath which is a solution comprising 50 wt. % of acrylonitrile, 1 wt. % of benzoyl peroxide, and 5 wt. % of Noigen SS emulsifier (a nonylphenol type of nonionic surfactant, manufactured by Daiichi Kogyo Seiyaku, Ltd.) based upon the weight of said fiber. The ratio of the fiber weight to the weight of the bath is 1:15. The solution is gradually heated up to 105° C. from room temperature and the fiber is heat treated at that temperature for 90 minutes.

After the heat treatment, the fiber is rinsed well in cold water to completely remove any non-reacted matters, by-products, and catalyst.

Next, the cleaned fiber is immersed in a bath which is a water solution comprising 10 wt. % of cupric sulfate, 10 wt. % of sodium thiosulfate, and 10 wt. % of hydroxylamine sulfate based upon the weight of the fiber. The ratio of the fiber weight to the bath weight is 1:20. The bath is gradually heated up to 100° C. from room temperature. The bath is heat treated at 100° C. for 60 minutes. After the heat treatment, the fiber is rinsed well in cold water and is dried completely.

The treated polyester fiber hasan olive color and its electrical resistivity was found to be $2 \times 10^{-1}$ Ω-cm.

Additionally, it was found that the acrylonitrile used for the treatment of the fiber was introduced into said polyester fiber in an amount of 8.2 % by weight of the fiber through the graft polymerization mentioned above.

EXAMPLE 15

Polyester fiber grafted with cyanic radical in the same manner as in Example 14 is immersed in a bath which is a water solution comprising 15 wt. % of cupric chloride and 7.5 wt. % of hydroxylamine sulfate, based upon the weight of the grafted fiber. The ratio of the weight of the fiber to the weight of the bath is 1:15. The fiber is heat treated at a bath temperature of 100° C. for 60 minutes.

After the heat treatment, the fiber is rinsed well in cold water and then is immersed in a bathwhich is filled with a water solution comprising 8 g/l of sodium thiosulfate, 8 g/l of citric acid, and 20 g/l of disodium hydrogen phosphate. The ratio of the fiber weight to the weight of the bath is 1:15. The fiber is heat treated at a bath temperature of 100° C. for 90 minutes. After the heat treatment, the fiber is rinsed well in cold water and then is dried completely.

The treated polyester fiber hasan olive-green color and its electrical resistivity was found to be $3 \times 10^{-1}$ Ω-cm. The content of copper sulfide was found to be 3.0 % by weight.

EXAMPLE 16

Rayon staple (2 denier, cut length 51 mm, Type KRP, manufactured by Kojin, Ltd.) is immersed in a bath which is a water solution of 2 wt. % of sodium hydroxide. The bath is kept at room temperature for 15 minutes and then the fiber is squeezed by means of mangles to 100 % of wet pickup.

Next, said fiber treated as mentioned above is immersed in a bath which is a solution comprising 50 g/l of acrylonitrile. The ratio of the fiber weight to the weight of the bath is 1:20. The bath is kept at a temperature of 55° C. for 90 minutes for additional treatment of the fiber.

Then, after neutralizing the fiber with alkali, any nonreacted matters and by-products are removed from it completely.

The cyanoethylized ratio through the reaction mentioned above was found to be 8 %.

The treated fiber is then immersed in a bath which is filled with a water solution comprising 10 wt. % of cupric sulfate, 10 wt. % of sodium thiosulfate, and 5 wt. % of hydroxylamine sulfate based upon the weight of the fiber. The ratio of the fiber weight to the weight of the bath is 1:20. The fiber is treated at a bath temperature of 80° C. for 90 minutes and then is rinsed well in cold water and dried completely.

The fiber obtained thereby exhibits an electrical resistivity of 1.0 Ω-cm and the content of copper sulfide is 2.8 % by weight.

Also, in treating cupro-ammonium fiber in place of the rayon staple mentioned above, the same result as that obtained above has been obtained.

EXAMPLE 17

After adjusting the pH of a water solution comprising 50 g/l of dicyandiamide and 300 g/l of formalin (formaldehyde 30 % of water solution) to be pH 10 with sodium carbonate, it is subjected to a methylol reaction at a temperature of 80° C. for 3 hours to obtain a reaction product for use in the treatment of cotton.

Cotton which is scoured through immersion in a bath which is filled with a water solution comprising 10 g/l of sodium hydroxide kept at a temperature of 100° C. for 60 minutes is cooled and immersed in another bath which is filled with a water solution comprising 100 g/l of said reaction product and 10 g/l of ammonium chloride at room temperature. Then, it is squeezed by means of mangles to 90 % of wet pickup and is preliminarily dried at a temperature of 80° C. Then, the cotton is subjected to heat treatment at a temperature of 180° C. or 3 minutes.

The heat treated cotton is immersed in a bath which is a water solution comprising 15 wt. % of cupric sulfate, 10 wt. % of sodium thiosulfate, and 10 wt. % of sodium hydrogen sulfite based upon the weight of the cotton. The ratio of the weight of the cotton to the weight of the water solution is 1:20. The water solution is gradually heated up to 80° C. from room temperature and it is kept at that temperature for 90 minutes for treatment of the cotton. The treated cotton is rinsed well in cold water and is dried completely.

The cotton fiber obtained thereby exhibits a khaki color and its electrical resistivity was found to be 3.6 Ω-cm. The content of copper sulfide was found to be 2.5% by weight.

EXAMPLE 18

Wool (64's Top) is rinsed well in a bath which is filled with a solution comprising 2 ml/l of Noigen SS (Nonyl phenol type of nonionic surfactant, manufactured by Daiichi Kogyo Seiyaku, Ltd.) at a temperature of 60° C. to remove any oil and grease from it. Then, it is immersed in a bath which is a solution comprising 50 wt. % of acrylonitrile, 1.2 wt. % of ammonium persulfate, and 3 wt. % of sodium hydrogen sulfite based upon the weight of the wool. The ratio of the weight of the wool to the weight of the bath is 1:20. The bath is gradually heated up to 60° C. from room temperature, and the wool is treated at that temperature for 90 minutes. After the treatment, the wool is rinsed well in warm water and then in cold water to completely remove any unreacted materials, by-products, and catalysts from it.

Then, the cleaned wool is immersed in another bath which is a water solution comprising 10 wt. % of copper sulfate and 10 wt. of sulfuric acid and 80 wt. % of copper sieve (No. 31, 21 mesh) based on the weight of the wool. The ratio of the wool weight to the bath weight is 1:15. The wool is treated in the bath at a temperature of 100° C. for 90 minutes and then is rinsed well in cold water.

The treated wool is then immersed in another bath which is a water solution comprising 10 g/l of sodium dithionite. The ratio of the wool weight to the weight of the bath is 1:15. The wool is treated in the bath at 100° C. for 60 minutes.

The wool fiber obtained exhibits an olive color and its electrical resistivity was found to be $5.5 \times 10^{-2}$ Ω-cm. The content of copper sulfide was found to be 5.2 % by weight.

EXAMPLE 19

Silk yarn is scoured by immersing it in a bath which is a water solution of 2 % sodium hydroxide at room temperature for 15 minutes. Then, it is squeezed by means of mangles to 40 % of wet pickup. The scoured silk yarn is immersed in another bath which is a solution comprising 50 g/l of acrylonitrile. The ratio of the yarn weight to the weight of the bath is 1:20. The yarn is treated in the bath at a temperature of 55° C. for 90 minutes.

Without drying, the treated silk yarn is neutralized of its alkalinity. Then, it is rinsed with cold water to completely remove any unreacted materials and by-products.

Next, the treated silk yarn is immersed in another bath which is a water solution comprising 5 wt. % of cupric chloride, 10 wt. % of sodium dithionite, and 10 wt. % of sodium hydrogen sulfite based upon the weight of the yarn. The ratio of the weight of the yarn to the weight of the bath is 1:20. The yarn is treated in the bath at 100° C. for 60 minutes. Then, the yarn is rinsed well in cold water and then is dried completely.

The silk yarn obtained thereby exhibits an olive color and its electrical resistivity was found to be $2.1 \times 10^{-1}$ Ω-cm. The content of copper sulfide was found to be 3.3 % by weight.

Each of the conducting fibers obtained in Examples 12 through 19 were subjected to X-ray analysis as in Example 11. The line of diffraction (Interfacial distance: 1.97 U, 3.21 U, and 2.79 U) of digenite (empirical formula: $Cu_9S_5$) was also found for each of the conducting fibers of Examples 12-19.

EXAMPLE 20

A polyacrylonitrile film having a thickness of 0.02 mm and a diameter of 7.5 cm and weighing 0.1 g was immersed in 100 ml of an aqueous bath containing 30 g/l of disodium hydrogen phosphate, 12 g/l of citric acid, 20 g/l of cupric sulfate, 10 g/l of sodium thiosulfate and 20 g/l of sodium hydrogen sulfite, and heat-treated in the bath at 60° C. for 3 hours to obtain a transparent, lightbrown film having a surface resistivity of 300 Ω. The surface resistivity herein and hereinafter was measured in accordance with the method stipulated in Japanese Industrial Standard K 6911. The film had the following infrared reflection characteristics:

| Wavelength (nm) | Reflectivity (%) |
|---|---|
| 800 | 18 |
| 1000 | 9 |
| 1500 | 7.5 |
| 2000 | 9 |
| 2500 | 9 |

X-ray diffraction pattern of the electrically conducting film showed strong diffraction at 1.97, 2.79 and 3.21 U typical to digenite, and weak diffraction at 1.88 and 2.40 U typical to chalcocite.

EXAMPLE 21

A polyacrylonitrile film having a thickness of 0.13 mm and a diameter of 7.5 cm and weighing 0.65 g was immersed in 200 ml of an aqueous bath containing 10 g/l of cupric sulfate and 10 g/l of hydroxylamine chloride. The bath was gradually heated up to 80° C. from room temperature and maintained at that temperature for 2 hours. After being washed with water, the resulting film was immersed in 200 ml of another aqueous bath containing 10 g/l of sodium dithionite, 30 g/l of disodium hydrogen phosphate and 8 g/l of sodium citrate. The bath was gradually heated up to 70° C. from room temperature and maintained at that temperature for one hour. The X-ray diffraction examination revealed that copper sulfide adsorbed by the film was composed mainly of a mixture of digenite and chalcocite. The film was found to have a surface resistivity of 160 Ω and exhibit infrared reflection similar to the film of Example 20.

EXAMPLE 22

A polyhexamethylene adipamide film (BO #15, manufactured by Toray Co., Ltd.) having a thickness of 15 μm and a size of 70×47 cm and weighing 5.0 g was immersed in 200 ml of an aqueous solution containing 10 g/l of ammonium persulfate and 10 g/l of sodium hydrogen sulfate at room temperature for 30 min. for chemical etching. The thus treated film was then placed in a stainless steel vessel to which was charged acrylonitrile vapor film at 38°-40° C. for 3 hours. The film having cyanic groups introduced thereinto was increased by 33 % in thickness and 32.8 % in weight. The resulting film was then immersed in a bath having the same composition as that of Example 20 for treatment at 55° C. for 2 hours, thereby to obtain a transparent, gold-brown film having a surface resistivity of 200 Ω. The film was found to absorb infrared rays similar to the film of Example 20. The X-ray diffraction examination revealed that the copper sulfide formed on the film was a mixture of digenite and chalcocite.

EXAMPLE 23

An acrylonitrile-butadiene-styrene copolymer plate having a thickness of 2 mm and a size of 9×2.5 cm and weighing 5 g was treated in a 62.5 % sulfuric acid saturated with potassium bichromate at 60° C. for one hour for chemical etching. The treated plate was, after being washed with water, then immersed in 200 ml of an aqueous bath containing 20 g/l of disodium hydrogen phosphate, 8 g/l of citric acid, 20 g/l of cupric sulfate and 20 g/l of sodium dithionite, and treated therein at 40° C. for 5 hours. The thus treated plate was dark gray in color and had a surface resistivity of 240 Ω. The X-ray diffraction pattern of the plate showed that the copper sulfide was formed mainly of digenite and a small amount of covellite. The plate was able to absorb infrared rays similar to the film of Example 20.

EXAMPLE 24

A polyethylene terephthalate film having a thickness of 12 μm and a size of 76×47 cm and weighing 5 g was treated in 200 ml of an aqueous solution containing 100 g/l of acrylonitrile, 4 g/l of benzoyl peroxide and 10 g/l of an emulsifier (PLYSURF A217E, manufactured by Daiichi Kogyo Seiyaku K.K.) at 105° C. for 90 min so that the acrylonitrile was grafted onto the polyester film. After being washed with water, the resulting film was treated in 200 ml of an aqueous bath containing 30 g/l of disodium hydrogen phosphate, 10 g/l of cupric sulfate, 10 g/l of sodium thiosulfate and 10 g/l of sodium hydrogen sulfite at 70° C. for 2 hours, thereby to obtain a light brown film having a surface resistivity of 420 Ω. The infrared absorption characteristics of the film resembled the film of Example 20. The X-ray diffraction examination indicated that the film was formed mainly of digenite.

EXAMPLE 25

A polyacrylonitrile film having a diameter of 9 cm and a thickness of 0.13 mm and weighing 1.0 g was immersed in 200 ml of an aqueous bath containing 10 g/l of cupric sulfate and 10 g/l of hydroxylamine. The bath was gradually heated from room temperature to 80° C. and maintained at that temperature for 2 hours. After being washed with water, the thus treated film was placed in a vessel charged with 0.5 Kg/cm²G of sulfur dioxide and 0.5 Kg/cm²G of steam for reaction between the monovalent copper ion-carrying film and sulfur dioxide at 105°-110° C. for 90 min. There was obtained a transparent, light brown film having a surface resistivity of 600 Ω. The film was able to absorb infrared rays to the same degree as the film of Example 20. The X-ray diffraction examination revealed that the film was formed mainly of digenite.

EXAMPLE 26

Polyac.ylonitrile threads (Silpalon, 100 denier, 40 manufactured by Mitsubishi Rayon K.K.) were immersed in an aqueous bath containing 20 g/l of cupric sulfate, 20 g/l of sodium thiosulfate and 10 g/l of sodium hydrogen sulfite with a ratio by weight of the threads to the bath being 1:20. The bath was then gradually heated from room temperature up to 50° C. at a heat up rate of ° C./min and maintained at that temperature for 3 hours. The thus treated threads were then washed with water and dried. The dried threads were found to have a specific resistivity of $3.6 \times 10^{-1}$ Ω-cm and to contain digenite. The threads were then knitted to obtain an electrically conducting fabric whose infrared ray absorbing characteristics were as follows:

| Wavelength (nm) | Reflectivity (%) |
| --- | --- |
| 800 | 10 |
| 1000 | 6.3 |
| 1500 | 6.2 |
| 2000 | 7.3 |
| 2500 | 8.4 |

EXAMPLE 27

Cashmilon (acrylic fiber) was treated in a bath containing 20 g/l of cupric sulfate, 20 g/l of sodium thiosulfate and 10 g, of sodium hydrogen sulfite at 20° C. for 12 hours. The resulting fiber, after being washed and dried, was then cut into a length of 0.5 mm and mixed into a commercially available acrylic paint (Acrylite No. 500, manufactured by Nippon Yushi Co., Ltd.) in an amount so that the content of the fiber in the resulting paint was 30 wt. %. The paint was applied onto a wood plate in an amount of 1200 g/m² (dry basis) and dried. The dried coating was found to have a surface electric resistivity of $3.5 \times 10^4$ Ω and showed excellent radiowave-absorbing properties. The transmission attenuation coefficient was −18 dB.

EXAMPLE 28

Phthalonitrile crystals were ground to a particle size of 10 μm or less and 10 g of the ground phthalonitrile powder were treated in 1000 ml of a bath containing 20 g/l of cupric sulfate, 20 g/l of sodium thiosulfate, 20 g/l of sodium hydrogen sulfite, 30 g/l of disodium hydrogen phosphate and 12 g/l of citric acid, at 50° C. for 3 hours. The resulting powder was washed with water and dried to obtain 11.1 g of copper sulfide-carrying phthalonitrile powder. The electrically conducting powder was then incorporated into a commercially available acrylic paint (Acrylite No. 500) with a mixing ratio by 1:1. The resulting paint was coated on an iron plate. The coating was found to have a surface electric resistivity of $2 \times 10^2$ Ω and a reflection attenuation coefficient of −25 dB. The coated iron plate was usable as a material for preventing radiowave reflection.

EXAMPLE 29

Polyacrylonitrile powder was ground to a particle size of 10 μm or less and the ground powder was treated in the same manner as that in Example 28. The thus obtained copper sulfide-carrying polyacrylonitrile powder was added into a vinyl chloride melt. The resulting melt containing 5 wt. % of copper sulfide-carrying polyacrylonitrile was then injected onto the surface of gloves formed of cotton. The gloves were effective in preventing problems caused by electrostatic charge.

We claim:

1. An electrically conducting material comprising a cyanic group-containing material having adsorbed thereby copper sulfide, wherein said cyanic group-containing material includes a water-insoluble compound selected from the group consisting of phthalonitrile, isophalonitrile, N-cyanomethylaniline, and N-beta-cyanoethylaniline.

2. A process for the preparation of an electrically conducting material, comprising treating a cyanic group-containing material with a soruce of monovalent copper ions and a sulfur-containing compound to adsorb copper sulfide by the cyanic group-containign material, wherein said cyanic group-containing material includes a water-insoluble compound selected from the group consisting of phthalonitrile, isophthalonitrile, N-cyanomethylaniline, and N-beta-cyanoethylaniline.

* * * * *